(12) United States Patent
Schürenberg et al.

(10) Patent No.: US 11,781,952 B2
(45) Date of Patent: Oct. 10, 2023

(54) HUMIDITY STABILIZATION DURING THE PREPARATION OF BIOLOGICAL SAMPLES FOR SPECTROMETRY

(71) Applicant: Bruker Daltonics GmbH & Co. KG, Bremen (DE)

(72) Inventors: Martin Schürenberg, Tarmstedt (DE); Sören-Oliver Deininger, Leipzig (DE); Alice Ly, Bremen (DE)

( * ) Notice: Subject to any disclaimer, the term of this patent is extended or adjusted under 35 U.S.C. 154(b) by 0 days.

(21) Appl. No.: 18/059,166

(22) Filed: Nov. 28, 2022

(65) Prior Publication Data

US 2023/0089846 A1 Mar. 23, 2023

Related U.S. Application Data

(63) Continuation of application No. 16/625,600, filed as application No. PCT/EP2018/068067 on Jul. 4, 2018, now Pat. No. 11,519,828.

(30) Foreign Application Priority Data

Jul. 12, 2017 (DE) .......................... 102017115598.8
Aug. 30, 2017 (DE) .......................... 102017119868.7

(51) Int. Cl.
*G01N 1/28* (2006.01)
*G01N 1/40* (2006.01)
*G01N 33/68* (2006.01)
*H01J 49/04* (2006.01)

(52) U.S. Cl.
CPC ............ *G01N 1/28* (2013.01); *G01N 1/4044* (2013.01); *G01N 33/6851* (2013.01); *H01J 49/0418* (2013.01)

(58) Field of Classification Search
CPC ..... G01N 1/28; G01N 1/4044; G01N 33/6851; H01J 49/0418
See application file for complete search history.

(56) References Cited

U.S. PATENT DOCUMENTS

| 11,519,828 | B2 * | 12/2022 | Schürenberg | G01N 33/6851 |
| 2006/0172332 | A1 * | 8/2006 | Vodyanoy | A01N 1/02 435/7.1 |
| 2014/0318959 | A1 * | 10/2014 | Yang | G01N 17/04 204/404 |

(Continued)

*Primary Examiner* — David A Vanore
(74) *Attorney, Agent, or Firm* — BENOIT & COTE, INC.

(57) ABSTRACT

The invention proposes preparing biological samples for spectrometry which contain cell structures and/or whole cells of human or animal origin (e.g. thin human and animal tissue sections) or prokaryotes (e.g. microorganisms), and which require constant relative humidity, in a temperature-controlled gas volume whose humidity is determined by a saturated substance solution, for example a suitable salt solution. The invention exploits a physico-chemical phenomenon called "deliquescence", which manifests itself by keeping the relative humidity above the saturated substance solution constant with a high degree of precision when a specified temperature is maintained. Pure succinic acid exhibits deliquescence at approx. 99% relative humidity, for example. Since an enormous variety of deliquescent salts and other suitable substances are available, it is possible to find the suitable substance for almost any desired relative humidity, with adjustment of the temperature, where necessary.

20 Claims, 4 Drawing Sheets

(56) References Cited

U.S. PATENT DOCUMENTS

2015/0093780 A1* 4/2015 Schurenberg ............ G01N 1/30
                                                    435/40.52
2016/0298164 A1* 10/2016 Sparbier ................... C12Q 1/18
2017/0067906 A1* 3/2017 Caprioli ............. G01N 33/6851

* cited by examiner

HUMIDITY STABILIZATION DURING THE PREPARATION OF BIOLOGICAL SAMPLES FOR SPECTROMETRY

BACKGROUND OF THE INVENTION

Field of the Invention

The invention relates to stabilization of the relative humidity in ambient gas during sample preparation of prokaryotes and cells of human or animal origin for spectrometric analysis, for example human and animal tissue samples for analysis with imaging mass spectrometry. To give an example: A preparation including enzymatic digestion of the linked proteins in thin human and animal tissue sections with chemical fixation (e.g. formaldehyde fixation) requires high humidity for the tissue to swell, which is necessary for the enzymes to act. At the same time, as little condensation as possible should be produced in this process so that the spatial resolution of the image is not adversely affected beyond the swelling.

Description of the Related Art

In pathology, the usual procedure is to fix tissue samples with formaldehyde to protect them against self-digestion, and to embed them in a water-insoluble substance, usually paraffin, to protect them against bacteria. Millions of well-characterized FFPE tissue samples which have been made storable in this way (FFPE=formalin-fixed, paraffin-embedded) are stored in pathological institutes and departments.

These samples represent an inexhaustible source for self-learning categorization processes and other analyses of thin tissue sections, particularly using methods of imaging mass spectrometry. However, the linkages of the proteins in the thin tissue sections have to be broken up again, and large proteins have also to be fragmented to make them detectable in the first place. This can be done by means of enzymatic digestion, for example, although lateral transport of the digest molecules by diffusion in excess liquids in the tissue should be avoided in order to maintain the positional accuracy of the proteins and thus the spatial resolution of the image.

The usual method of preparing an FFPE thin tissue section comprises the following steps: (a) Mount the section onto the specimen slide or sample support; (b) Deparaffinize; (c) "Antigen retrieval", basically a heat treatment or other energy treatment to partially break open formalin-induced cross-links; (d) Spray on the enzyme (in a digest buffer, usually ammonium bicarbonate); (e) Incubate in a humid atmosphere; (f) Dry; (g) Spray on the matrix solution; and (h) Measure (see for example EP 1 695 062 B1; "Analysis of chemically cross-linked tissue samples by mass spectroscopy", C. Conklin and P. J. Parks).

Enzymatic digestion of a thin tissue section by means of trypsin, for example, requires the thin section to have a high moisture content, i.e. a high swelling, in order for the enzyme applied to be able to diffuse into the thin section and act. This can be achieved when the ambient air has a relatively high level of humidity, although it should remain below the dew point because uncontrolled condensation of liquid on the thin tissue section leads immediately to lateral transport of molecules and can drastically reduce the spatial resolution of the imaging mass spectrometry. The level of humidity may have to be maintained for hours and, depending on the temperature, which is usually set to between 37° C. and 50° C., digestion times of up to 20 hours may be necessary for optimum results.

Enzymatic digestion of proteins or other molecules of a thin tissue section is not limited to formaldehyde-fixed tissue samples, however. Digestion of extremely large molecules which are to be analyzed by means of ionization using matrix-assisted laser desorption (MALDI), or another method of ionization/detection, can also be suitable for thin tissue sections which are not fixed. It can also be useful to remove the residual glycan from proteins by enzymatic digestion and subsequently measure the residual glycans which are released.

As shown schematically in FIG. 1, the mass spectrometric image quality improves at an increasing rate with increasing humidity during sample preparation until a drastic drop in the image quality occurs when the dew point of 100% relative humidity is reached. The image quality is a complex mix of image contrast, spatial resolution of the image and other parameters, while the drop in image quality is mainly attributable to a loss of spatial resolution of the image. The drop in spatial resolution of the image is mainly caused by the lateral transport of analyte molecules in or on the thin tissue section by diffusion in liquid. To make the analyte molecules contained in the tissue completely accessible and with maximum possible positional accuracy, it is therefore very important, in this example, to use a relative humidity as close as possible to 100 percent without exceeding this limit. This is very difficult to control with the methods currently being used because, at a humidity of approximately 100%, the slightest inhomogeneities in temperature, or dynamic effects in the humidity chamber, can lead to uncontrollable condensation.

The fact that a company (SunChrom GmbH, 61381 Friedrichsdorf/Germany) has marketed an instrument (SunDigest) specifically designed for this purpose also illustrates the need for stable enzymatic digestion methods for the preparation of samples in imaging mass spectrometry (www.sunchrom.de/suncollect/sundigest). The instrument measures and controls the humidity in a complex procedure but remains below 95% humidity on average due to the unavoidable control oscillations (hunting).

The company Quantifoil Instruments GmbH (07749 Jena/Germany) supplies a cassette called μBOX for the incubation of specimen slides for microscopy or microtitration plates under humid conditions. In the μBOX, a damp sponge or damp paper can provide humidification, but the lack of temperature control means it is not supervised.

The paper "Mass Spectrometric Imaging of Wheat (*Triticum* spp.) and Barley (*Hordeum vulgare* L.) Cultivars: Distribution of Major Cell Wall Polysaccharides According to Their Main Structural Features" by D. Velickovic et al. (J. Agric. Food Chem. 2016, 64, pages 6249-6256) describes in-situ digestion of cell wall polysaccharides. Enzymes, such as xylanase or lichenase, are homogeneously applied to the grain sample surface as fine droplets using a spraying robot. After spraying, the grain samples are transferred to a closed container maintained at a controlled relative humidity of 96.4±0.4% and then incubated at 40° C. for 4 hours.

Other types of sample for mass spectrometric analysis may also require a stable level of humidity, however. If, for example, microbes are incubated in tiny droplets of a nutrient solution on the mass spectrometric sample support, this may take several hours, and therefore high humidity is necessary to ensure that the droplets do not dry up. Incubation is particularly useful when analyzing the microbes' ability to grow in the presence of certain antibiotics, as it allows their resistance to these antibiotics to be determined (see for example EP 3 081 652 A1 "Rapid Testing of Resistances by means of Mass Spectrometry", K. Sparbier and B. Wegemann).

Infrared spectrometry on tissue or microbial samples may also require the humidity to be kept constant, but in this case at a set value preferably in the range between 10% and 30% relative humidity. Only when the humidity is precisely set and maintained, can the spectra be accurately reproduced and reliably compared with reference spectra.

Given the explanations above, there is still a need for simple methods and devices which provide stable humidity for the sample preparation of prokaryotes and cells of human or animal origin in spectrometry, particularly thin human and animal tissue sections, tissue extracts of human or animal origin, microorganism cultures and other organic samples.

SUMMARY OF THE INVENTION

The term "samples" here shall designate solely biological samples which contain cell structures and/or whole cells of human and animal origin or prokaryotes, for example thin human and animal tissue sections or accumulations of microorganisms, such as including but not being limited to bacteria and fungi, and thus differ from individual cell components at the molecular level (e.g. artificially synthesized nucleic acid strands, which are used as genetic probes in hybridization reactions). Tissue can be understood to be an ensemble of similar cells from the same origin, such as a living being, that together carry out a specific function. These biological samples of human and animal origin are characterized by the fact that they can swell or dry up to differing degrees, depending on the ambient conditions. When preparing these samples, it is therefore usually important to keep the humidity around the sample constant, and often the humidity level must be precisely reproducible. The cell structure of human or animal tissue, for example, is characterized by cut tissue cells which lie at the cut surfaces of a thin tissue section.

The invention exploits a physico-chemical phenomenon called "deliquescence". The deliquescence manifests itself through the fact that the relative humidity in a gas volume above a saturated solution of a suitable substance can be kept constant with a high degree of precision when a specified temperature is maintained. The substances are usually salts. For example, a humidity of around 98.0% is maintained above a saturated solution of potassium sulfate ($K_2SO_4$) in water at 37° C.; at 50° C. it is approx. 97.2%. Substances which are not salts may also exhibit deliquescence, however. Pure succinic acid exhibits deliquescence at approx. 99% relative humidity, for example. In the following, the terms "salt" or "salt solution" are often used for simplicity. It shall be understood, however, that deliquescent substances which are not salts are also included.

The invention now proposes that samples for spectrometry which require stable humidity, such as samples of human and animal origin or prokaryotic samples, should be prepared in a temperature-controlled gas volume. The gas volume can be located above a saturated salt solution, or it can be fed with a moist gas flow which has been brought to a predetermined relative humidity by interaction with a saturated salt solution (e.g. in an upstream chamber). The preparations can relate to the enzymatic digestion of frozen or chemically fixed (e.g. formaldehyde-fixed) thin human and animal tissue sections, for example, which are to be analyzed with imaging mass spectrometry, or in general the digestion of large molecules in human and animal tissue samples, e.g. with the objective of splitting off residual glycans (eukaryotic samples), or the incubation of microbes in droplets of nutrients on a sample support plate (prokaryotic samples). If a relative humidity above 97% is required, for example, then a saturated solution of potassium sulfate or succinic acid is suitable in the generally used temperature range between 37° C. and 50° C. Since an enormous variety of salts are available, it is possible to find the salt which is suitable for any desired relative humidity, with adjustment of the temperature conditions, where necessary.

Preparation of the biological sample preferably takes place under humidity-controlled conditions on the same sample support which subsequently serves as the substrate for a mass spectrometric or infrared-spectrometric measurement. For mass spectrometry, the sample support can take the form of a flat steel plate or ceramic plate/glass plate with a conductive coating, for example.

Furthermore, deliquescence can be used to create an air flow having the desired temperature and desired relative humidity, said air flow being fed into a chamber for the preparation of a biological sample, where it generates the desired conditions.

An instrument for the preparation of samples requiring humidity, such as human and animal thin tissue sections or microorganism cultures, can comprise a chamber containing a wide dish for the saturated salt solution in a closed gas volume, having a holder for the sample on a suitable substrate above the salt solution, and a temperature control device for the salt solution and for all the walls of the chamber to avoid any condensation of water and any droplet formation.

In general, the invention relates to methods for the preparation of biological samples such as samples of human and animal origin or prokaryotic samples for spectrometric analysis and is characterized by the fact that the preparation takes place in a gas volume in which the humidity is kept constant by deliquescence.

The preparation can in particular relate to the chemical or enzymatic conversion of molecules in human and animal tissue samples, such as tissue extracts or thin tissue sections for analysis with imaging mass spectrometry, where a set humidity value creates a desired degree of swelling of the tissue, which is advantageous for the chemical or enzymatic reactions, while largely maintaining the positional accuracy of the molecules. The swelling of the tissue can be supported by applying a measured quantity of a hygroscopic substance (e.g. glycerin). The tissue can be a thin human or animal tissue section on a sample support which can be suitable for mass spectrometry (e.g. a metal plate, or a ceramic plate or glass plate coated with a conductive layer), and be chemically fixed (e.g. by formaldehyde) and, as the case may be, embedded in an organic solid substance, such as paraffin for instance. Imaging mass spectrometry (IMS) can work with ionization by matrix-assisted laser desorption (MALDI) in a time-of-flight (TOF) mass spectrometer, with desorbing electrospray ionization (DESI) or with secondary ion mass spectrometry (SIMS).

The preparation can, very generally, consist in macromolecules of the sample being broken into fragments by enzymatic digestion. But it may also involve living microbes which are incubated on a sample support plate in droplets of a nutrient liquid: see for example the international application WO 2018/099500 A1 (PCT/DE2016/100561). As the case may be, the droplets can contain measured quantities of anti-microbial substances, such as antibiotics and antimycotics, in order to allow for susceptibility testing.

A high level of humidity slightly below the dew point can be generated with this method, using a saturated solution of potassium sulfate $K_2SO_4$ or succinic acid $C_4H_6O_4$, for example. Here, a high level of humidity slightly below the dew point shall be taken to mean, in particular, a humidity of more than 95%. Lower humidity levels for special applications are also possible, for example using magnesium chloride hexahydrate $MgCl_2 \cdot 6H_2O$.

Preparation of microbial samples for infrared spectrometric analysis with the objective of identifying microbial subspecies or varieties similarly requires a precisely set relative humidity for the repeatability and comparability of infrared spectra, and this relative humidity, such as between about 10% and 30%, can be set and maintained using deliquescence.

DETAILED DESCRIPTION

The invention is based on "deliquescence", a relatively little known physico-chemical phenomenon. The deliquescence manifests itself here in that a gas volume above a saturated salt solution gives rise to a relative humidity that can be kept constant with high precision when a specified temperature is maintained. If the relative humidity in the gas volume increases, water condenses into the saturated solution, but the resulting higher degree of dilution is compensated by the dissolution of more salt. If the relative humidity in the gas volume decreases, water evaporates from the saturated solution, but the oversaturation thus created is reduced again by the recrystallization of the salt.

Deliquescence is not the same as hygroscopicity. Hygroscopic materials reduce the humidity by removing water from the ambient air, but this water is bound by the materials, for example as water of crystallization or in pores. This process is therefore not easily reversible, and is thus susceptible to failure if it is necessary to set and maintain constant humidity conditions.

Figure 2:
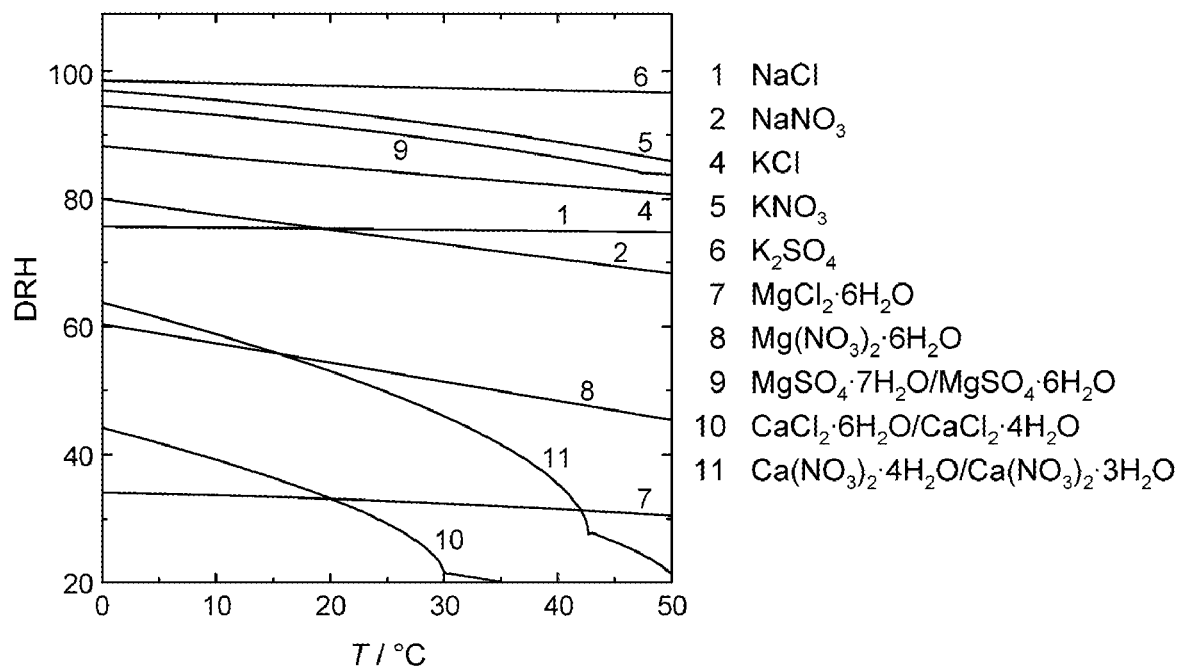
FIG. 2 shows the relative humidities (DRH—deliquescence relative humidity) above saturated solutions for different salts as preferred deliquescent substances (taken from SaltWiki).

Deliquescence is important in the building materials industry, which bears no relation to the field of the present disclosure, because it can cause moisture damage to buildings especially in freezing conditions. FIG. 2 depicts the deliquescence relative humidity (DRH) for several salts as a function of temperature.

The invention now proposes that sample preparation which requires a constant relative humidity should be carried out in a temperature-controlled gas volume in which the humidity is maintained at a constant value by deliquescence, for example in a gas volume above a saturated salt solution. Since an enormous variety of salts and other suitable (water-soluble) substances are available, it is possible to find the suitable substance for almost any desired relative humidity, using specific temperature settings, where necessary.

Figure 1:
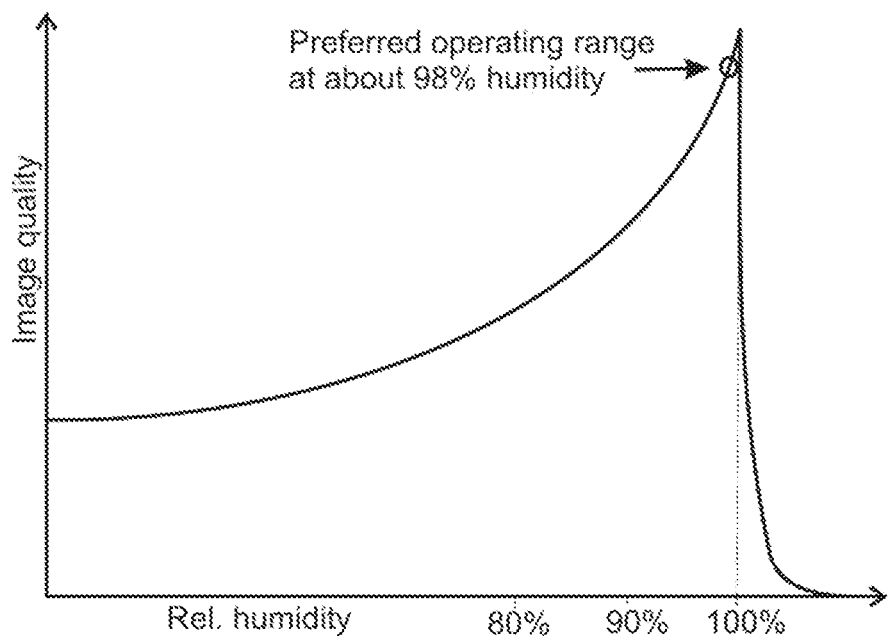
FIG. 1 shows the image quality of mass spectrometric images of tissue sections as a function of the relative humidity during preparation of the tissue sections using enzymatic digestion. The best image quality is achieved at high relative humidity slightly below the dew point (95%<rH<dew point), particularly because the digestion times necessary in this case can be kept relatively short and therefore the radius of the lateral material transport, which degrades the image quality, can be kept small.
Figure 3:
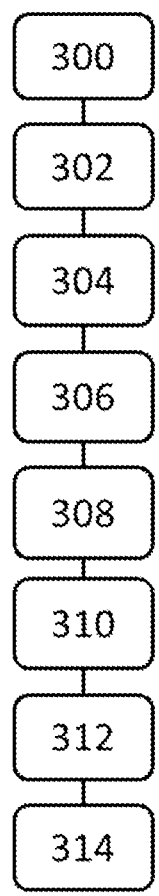
FIG. 3 presents a flow diagram of a procedure for preparing an FFPE thin human or animal tissue section for imaging mass spectrometry.

As can be seen from FIG. 1, high relative humidity just below the dew point is particularly important for the preparation of thin human and animal tissue sections including enzymatic digestion for imaging mass spectrometry. FIG. 3 shows a flow diagram of a possible procedure for preparing an FFPE thin human or animal tissue section that comprises the following steps. Step 300: Mount the section onto the specimen slide or sample support, e.g. a stainless steel plate; Step 302: Deparaffinize; Step 304: "Antigen retrieval", basically a heat treatment or other energy treatment to partially break open formalin-induced cross-links in the section; Step 306: Spray on the enzyme (in a digest buffer, usually ammonium bicarbonate), e.g. trypsin; Step 308: Incubate in a humid atmosphere close to the dew point maintained by deliquescence; Step 310: Dry; Step 312: Spray on the matrix substance, e.g. sinapinic acid, α-cyano-4-hydroxycinnamic acid (α-CHCA), or 2,5-dihydroxybenzoic acid (DHB); and Step 314: Measure a distribution chart of analytes of interest, such as peptides and proteins, from the prepared section mass spectrometrically, e.g. using MALDI TOF.

In the temperature range between 37° C. and 50° C., which is typically used for the digestion, a saturated solution of potassium sulfate ($K_2SO_4$), which maintains a humidity of around 98.0% at 37° C., and around 97.2% at 50° C., is suitable, for example (see curve 6 in FIG. 2). The times needed for a digestion leading to a quasi-optimal image are a few hours. At higher temperatures, which essentially entail higher (detrimental) diffusion rates for lateral molecular transport, shorter times are possible. The optimum temperatures and digestion times are preferably determined experimentally.

Figure 4:
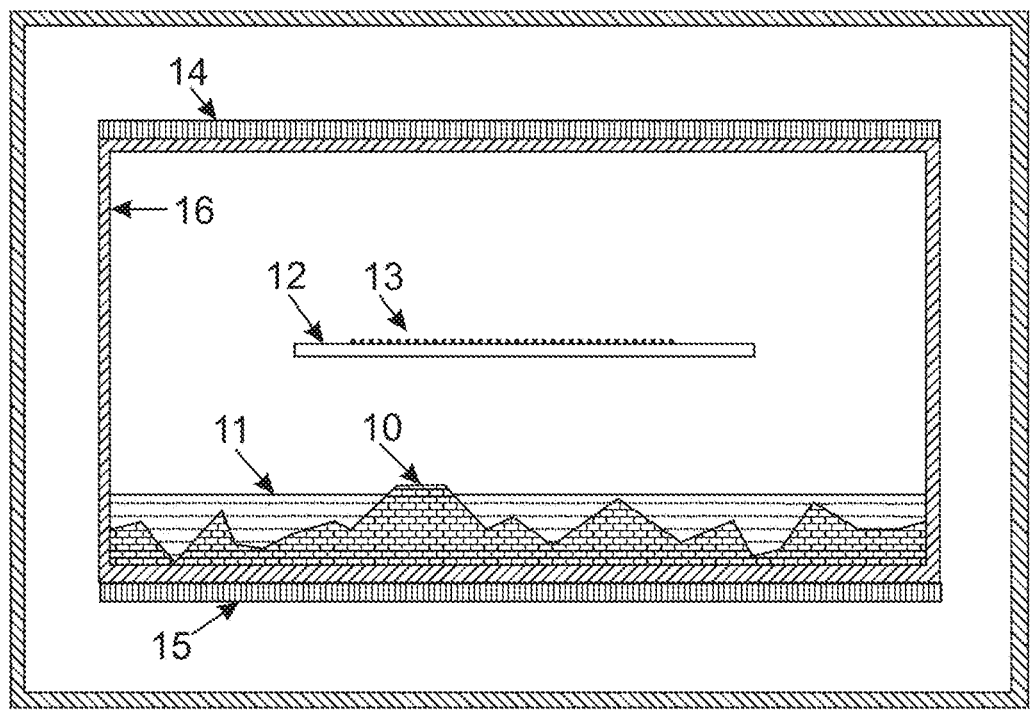
FIG. 4 shows a schematic representation of a thermally insulated chamber (16) including lid heating (14) and floor heating (15), whose floor is covered with crystalline salt (10) and a layer of water (11), for the preparation of a cell sample of human or animal origin or a prokaryotic sample (13) on a sample support (12), said sample requiring a specific humidity. The sample (13) can be a thin human or animal tissue section and the sample support (12) can be suitable for mass spectrometry (e.g. MALDI time-of-flight mass spectrometry).

FIG. 4 shows a rough schematic representation of a thermally insulated chamber (16) for the preparation of a cell sample of human or animal origin or a prokaryotic sample (13) on a sample support (12) which requires a specific humidity. The sample (13) can be a thin human or animal tissue section and the sample support (12) can be suitable for mass spectrometry (e.g. MALDI time-of-flight mass spectrometry). All holders for sample supports and chamber and all means of opening the chamber have been omitted for greater clarity. In this embodiment, two heating elements (14) and (15) heat the lid and the floor of the chamber. The floor is covered by crystalline or crystallized salt (10) and a saturated aqueous solution (11) of the salt. It does not matter if salt (10) protrudes from the solution. It is advantageous for the boundary surfaces between salt solution and air, and between solid salt to salt solution to be as large as possible. The aqueous solution should only form a comparatively thin layer so as to rapidly facilitate the compensation for evaporation or condensation by further dissolution or recrystallization of salt, without the salt molecules having to traverse long diffusion paths in the liquid. It is also possible to agitate the solution continuously (albeit gently), for example by stirring, preferably such that the formation of salt aerosol is avoided. For a similar reason, the gas in the chamber can also be carefully kept in motion, for example by a small fan (not shown).

The deliquescence maintains the gas volume above the saturated solution at constant humidity, and practically no measurable control oscillations exist. To disturb the equilibrium of the relative humidity as little as possible when the sample support is introduced and removed, it is favorable for the sample support (12), which has been brought up to temperature, to be introduced into/removed from the chamber (16) through a suitably designed lock.

Figure 5:
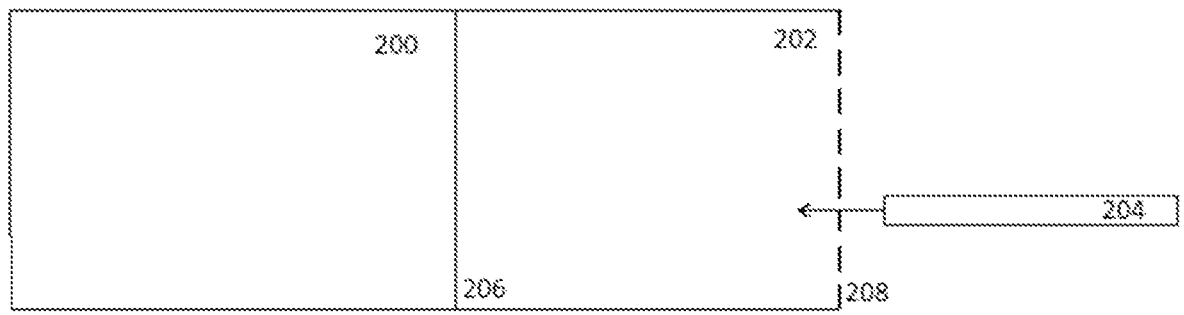
FIG. 5, panels A, B and C, illustrates the introduction of a sample support into an incubation chamber in which the humidity is stabilized by deliquescence using a lock.
Figure 5:
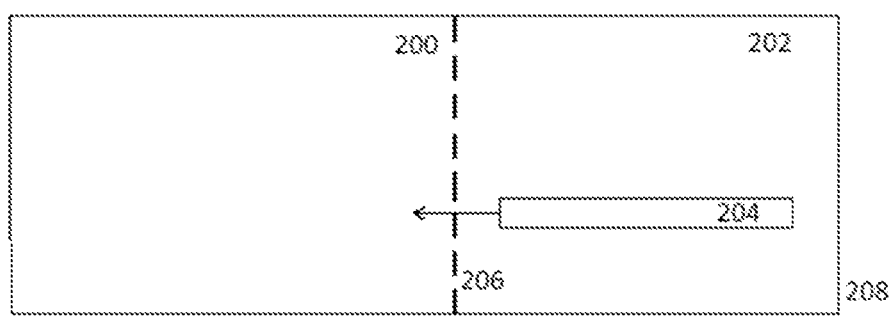
Figure 5:
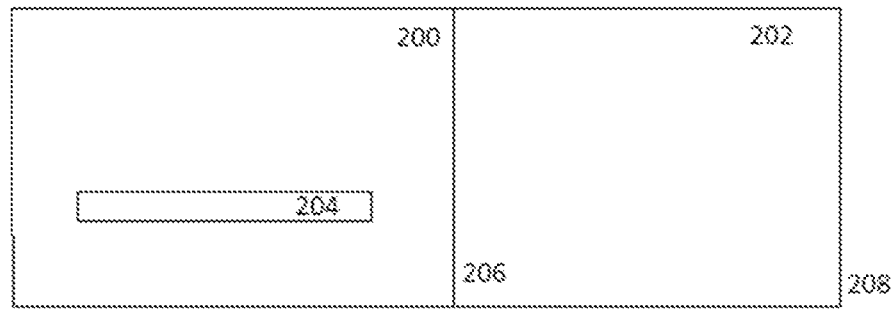

FIG. 5, panels A, B and C, shows schematically the introduction of a sample support (204) carrying the sample, such as a human or animal tissue section or a microorganism culture in droplets of liquid nutrient, into an incubation chamber (200). The incubation chamber (200) is kept at constant humidity by means of deliquescence and shut off from the ambient atmosphere by lock chamber (202) and gates (206) and (208). For introducing the sample support (204) into the incubation chamber (200) from outside, gate (208) is opened while gate (206) remains closed, panel A. Once the sample support (204) has reached the lock chamber (202), gate (208) is closed and the conditions in the lock chamber (202) are harmonized with that in the incubation chamber (200) in order to be able to introduce it without affecting the conditions in the incubation chamber (200). Then gate (206) is opened in order to transfer the sample support (204) from the lock chamber (202) into the incubation chamber (200), panels B and C. The perturbation of the gas atmosphere in the incubation chamber (200) during the introducing (and in reverse sequence also during the taking out) of the sample support (204) can be kept small by the attached lock chamber (202) and gates (206, 208).

If a lock is used for the introduction of the sample support, then the sample support carrying the sample is preferably first brought up to a temperature which is slightly above the temperature of the gas volume in order to prevent any condensation of water on the sample. This may take place in the lock, for example. If no lock is used, but instead a lid or a door to the chamber is opened, the humidity equilibrium is unavoidably disturbed initially. However, the disturbed humidity equilibrium can be used to bring the sample support, which is placed onto a solid holder at the target temperature, up to temperature before the humidity is restored again. For example, it is possible to equip the chamber with a lid or a door which can be controlled to close slowly. Condensation can also be avoided in this way.

Instead of the thermally insulated chamber, a chamber (16) which contains no heating elements and no external insulation can simply be placed into an incubator (indicated by the outer, hatched wall in FIG. 4).

With enzymatic digestion of the proteins of a thin tissue section, it is important that the thin tissue section is kept swollen as specified to allow the enzyme to penetrate into the thin section and act. The swelling is produced by the humidity but can also be improved by further measures. The application of a measured quantity of hygroscopic substances, for example glycerin, which is also familiar as a moisturizing agent in cosmetics, can increase the water content of the thin section. The hygroscopic substance can, for example, be sprayed on, highly diluted, together with the enzyme as a component of the enzyme buffer. The hygroscopic substance can, however, also be sprayed onto the thin section separately from the enzyme, in a rapidly evaporating solvent, for example acetone, in a carefully chosen dose.

If the temperature of the sample support bearing the thin tissue section is reduced below the dew point, droplets do not form immediately, but instead a cohesive film of water forms on the surface of the already swollen tissue. This can be utilized to increase the moisture in the tissue. The procedure sometimes slightly reduces the temperature of the sample support for a short time, but it immediately returns to the original temperature again. This can be achieved by a heating element, such as a Peltier element, under the sample support plate, for example. This method practically pumps a small amount of moisture into the tissue. The optimal parameters are preferably explored experimentally.

Other types of sample preparation for spectrometric analyses may also require stable humidity, however. If, for example, microbes have to be incubated for several hours in tiny droplets of a nutrient solution on the (flat) mass spectrometric or infrared spectrometric sample support, high humidity is necessary to ensure that the droplets do not dry up. On the other hand, uncontrolled condensation of water into the droplets should be avoided, too. In this case also, the deliquescence above a saturated solution of a suitable substance, e.g. potassium sulfate, proves to be advantageous and suitable. Incubation can serve to analyze the ability of the microbes to grow in the presence of specific antimicrobial substances such as antibiotics and antimycotics, while their resistance to these antimicrobial substances can be determined.

In addition to this preferable, stationary method of stabilizing the humidity, it is also possible to conceive other methods using deliquescence, for example a dynamic method where a little water vapor is continuously fed into the gas volume, while the excess moisture is continuously absorbed by the saturated solution.

A further, non-stationary method involves using deliquescence to bring a gas flow to a constant relative gas humidity and feeding this gas flow into a chamber in which the constant gas humidity is required for the preparation of biological samples. The gas flow can pass through a chamber containing a saturated solution, for example, as has been described above. The gas flow can, however, also be blown slowly, and in the form of small bubbles, through a gas washing bottle containing a saturated solution of a deliquescent substance, where a filter preferably cleans the gas flow of any entrained particles or droplets of solution. An impactor arrangement in the gas pipe can also be suitable to separate the humidified gas from any suspended particles of heavy substances.

The patent specification DE 10 2013 022 016 B4 (equivalent to WO 2015/090727 A1), "Microbe identification by mass spectrometry and infrared spectrometry", M. Kostrzewa, describes how IR spectrometry can be used for the identification of microbe subspecies or varieties. A method of exploring the subspecies level of *Yersinia enterocolitica* in a prevalence study using infrared spectrometry can be taken from I. Stamm et al., Journal of Clinical Microbiology, March 2013, Volume 51, Number 3, p. 887-893. It has meanwhile been found that it is necessary to keep the humidity constant when acquiring infrared spectra of samples containing tissues or microbes, but in this case at a set value specified for the method, preferably in the range between 10% and 30% relative humidity. Only when this humidity is precisely set, can the spectra be accurately reproduced and reliably compared with reference spectra which were acquired at the same relative humidity. If the humidity changes, the spectrum changes; if one returns to the specified humidity, the original IR spectrum returns also. In this case, a small air flow can be guided through a chamber which contains a saturated solution of a suitable substance having a large surface area, see for example curve 7 in FIG. 2 (magnesium chloride hexahydrate, $MgCl_2 \cdot 6H_2O$), and then the air flow can be fed at a set relative humidity to the sample in the infrared spectrometer. The sample here must be in a suitable vessel in order to seal it off from the ambient air. This type of identifying analysis of microbial subspecies and varieties is increasing in importance.

The types of application and embodiments described here form only a fraction of the possible methods which are made available by the invention. With knowledge of this disclosure, the person skilled in the art will easily be able to develop further advantageous embodiments for preparation methods of biological samples which contain cell structures and/or whole cells of human and animal origin and/or prokaryotes for spectrometric measurement while maintaining a specific, stable humidity, and these shall be included in the scope of protection of the claims, including any equivalent implementations as the case may be.

The invention claimed is:

1. A method for preparing a tissue section of human or animal origin for analysis using imaging mass spectrometry, comprising:
   providing the tissue section of human or animal origin;
   subjecting the tissue section to a preparation which renders it fit for a following analysis, wherein the preparation takes place in a gas-tight preparation chamber in which the relative humidity is kept constant, and wherein the preparation comprises chemical or enzymatic conversion of molecules in the tissue section, where a set level of humidity causes the tissue of the tissue section to swell to the desired extent, which is advantageous for the chemical or enzymatic reactions, while largely maintaining the positional accuracy of the molecules, and further wherein the swelling of the tissue is assisted by a hygroscopic substance which is applied to a surface of the tissue section in a measured quantity; and
   transmitting the prepared tissue section to analysis using imaging mass spectrometry.

2. The method according to claim 1, wherein the imaging mass spectrometry works with ionization by matrix-assisted laser desorption in a time-of-flight mass spectrometer.

3. The method according to claim 1, wherein the enzymatic conversion is effected using trypsin.

4. The method according to claim 1, wherein the hygroscopic substance is glycerin.

5. The method according to claim 1, wherein the tissue is provided in chemically fixed form, for example fixed by formaldehyde.

6. The method according to claim 5, wherein the tissue is provided embedded in an organic solid material, such as paraffin.

7. The method according to claim 1, wherein the tissue is provided in frozen form.

8. The method according to claim 1, wherein proteins contained in the tissue section are broken into fragments by enzymatic digestion.

9. The method according to claim 1, wherein, during preparation, the temperature of the tissue section is briefly reduced to below the dew point to facilitate the controlled formation of a cohesive film of moisture on the surface of the tissue section.

10. The method according to claim 1, further comprising setting a high level of humidity just below the dew point during the preparation.

11. The method according to claim 10, where the relative humidity is set to be equal to or higher than 95%.

12. The method according to claim 1, wherein the preparation of the tissue section takes place directly on a same sample support which subsequently serves as substrate for the analysis using imaging mass spectrometry.

13. The method according to claim 12, wherein the sample support takes the form of a flat steel plate, or flat ceramic plate/glass plate having a conductive coating.

14. The method according to claim 1, wherein the tissue section contains cell structures and/or whole cells of human or animal origin.

15. The method according to claim 1, wherein the humidity is kept constant using deliquescence.

16. The method according to claim 15, wherein the gas-tight preparation chamber comprises a holder for a sample support, a device for controlling the temperature of the chamber, and a dish for a saturated solution and a deliquescent substance to be dissolved.

17. The method according to claim 16, further comprising, during the preparation, gently agitating (i) the saturated solution and/or (ii) a gas in the gas-tight preparation chamber.

18. The method according to claim 15, wherein the gas-tight preparation chamber is supplied with a gas flow which has been brought to a specified relative humidity by interaction with a saturated solution of a deliquescent substance.

19. The method according to claim 1, wherein the sample support is introduced into, and removed from the gas-tight preparation chamber using a lock.

20. The method according to claim 1, wherein the hygroscopic substance is sprayed onto the surface of the tissue section (i) together with an enzyme as a component of an enzyme buffer, or (ii) separately from the enzyme, in a rapidly evaporating solvent.

* * * * *